(12) United States Patent
Wilkinson

(10) Patent No.: US 10,335,174 B2
(45) Date of Patent: Jul. 2, 2019

(54) SYSTEM AND METHOD FOR RE-ENTERING A VESSEL LUMEN

(71) Applicant: Cardinal Health Switzerland 515 GmbH, Baar (CH)

(72) Inventor: Matthew Wilkinson, Basking Ridge, NJ (US)

(73) Assignee: CARDINAL HEALTH SWITZERLAND 515 GMBH, Bar Zug (CH)

( * ) Notice: Subject to any disclaimer, the term of this patent is extended or adjusted under 35 U.S.C. 154(b) by 0 days.

(21) Appl. No.: 15/089,205

(22) Filed: Apr. 1, 2016

(65) Prior Publication Data

US 2016/0213386 A1    Jul. 28, 2016

Related U.S. Application Data

(60) Division of application No. 14/580,397, filed on Dec. 23, 2014, now abandoned, which is a continuation of application No. 13/232,115, filed on Sep. 14, 2011, now Pat. No. 8,920,449.

(Continued)

(51) Int. Cl.
*A61B 17/22* (2006.01)
*A61M 25/00* (2006.01)
(Continued)

(52) U.S. Cl.
CPC .......... *A61B 17/22* (2013.01); *A61B 17/3421* (2013.01); *A61M 25/007* (2013.01); *A61M 25/0082* (2013.01); *A61M 25/0194* (2013.01); *A61M 25/04* (2013.01); *A61M 29/02* (2013.01); *A61B 2017/00778* (2013.01); *A61B 2017/22001* (2013.01); *A61B 2017/22071* (2013.01); *A61B 2017/22094* (2013.01);
(Continued)

(58) Field of Classification Search
CPC ................ A61B 17/22; A61B 17/3421; A61B 2017/22095; A61M 29/02; A61M 25/007; A61M 25/0082; A61M 2025/0087; A61M 2025/0197
See application file for complete search history.

(56) References Cited

U.S. PATENT DOCUMENTS 5,127,917 A    7/1992  Niederhauser et al.
5,707,362 A    1/1998  Yoon
(Continued)

FOREIGN PATENT DOCUMENTS

JP    2008538190 A    10/2008
WO    2005049125 A1    6/2005

OTHER PUBLICATIONS

International Search Report and Written Opinion for Application No. PCT/US2012/043542, dated Oct. 11, 2012, 13 pages.
(Continued)

*Primary Examiner* — Anh T Dang
(74) *Attorney, Agent, or Firm* — Nada J. Ardeleanu

(57) ABSTRACT

This disclosure is directed to systems and methods for re-entering the true lumen of a vessel. The re-entry catheters employ deflectable struts to stabilize and support the distal tip in a subintimal location while a passageway back into the true lumen is formed. Re-entry to the true lumen can be effected with a cutting element or with a conventional guidewire.

11 Claims, 5 Drawing Sheets

Related U.S. Application Data

(60) Provisional application No. 61/502,684, filed on Jun. 29, 2011.

(51) Int. Cl.
*A61M 25/04* (2006.01)
*A61B 17/34* (2006.01)
*A61M 29/02* (2006.01)
*A61M 25/01* (2006.01)
*A61B 17/00* (2006.01)

(52) U.S. Cl.
CPC ............... *A61B 2017/22095* (2013.01); *A61B 2017/3409* (2013.01); *A61M 2025/0087* (2013.01); *A61M 2025/0096* (2013.01); *A61M 2025/0197* (2013.01); *Y10T 29/49609* (2015.01)

(56) References Cited

U.S. PATENT DOCUMENTS

| | | |
|---|---|---|
| 6,027,514 A | 2/2000 | Stine et al. |
| 6,663,577 B2 | 12/2003 | Jen et al. |
| 6,726,677 B1 | 4/2004 | Flaherty et al. |
| 7,179,270 B2 | 2/2007 | Makower |
| 2002/0072706 A1* | 6/2002 | Hiblar ............... A61M 25/0084 604/101.01 |
| 2003/0109809 A1 | 6/2003 | Jen et al. |
| 2006/0094930 A1 | 5/2006 | Sparks et al. |
| 2007/0093780 A1 | 4/2007 | Kugler et al. |
| 2008/0228171 A1 | 9/2008 | Kugler et al. |
| 2008/0243067 A1 | 10/2008 | Rottenberg et al. |
| 2008/0306499 A1 | 12/2008 | Katoh et al. |
| 2009/0230167 A1 | 9/2009 | Xiao et al. |
| 2010/0145265 A1* | 6/2010 | Min ............... A61M 25/0068 604/95.03 |

OTHER PUBLICATIONS

Office Action in corresponding Japanese Patent Application No. 2014-518663 dated Apr. 19, 2016.

Office Action for European Patent Application No. 12733322, dated Jul. 18, 2017, 4 pages.

* cited by examiner

SYSTEM AND METHOD FOR RE-ENTERING A VESSEL LUMEN

This application is a divisional application of and claims the priority of benefits under 35 USC § 119 and 120 from U.S. patent application Ser. No. 14/580,397 filed Dec. 23, 2014, which is a continuation of US patent application Ser. No. 13/232,115 filed Sep. 14, 2011, now U.S. Pat. No. 8,920,449, which Patent claims the priority benefits of U.S. Provisional Patent Application Ser. No. 61/502,684, filed Jun. 29, 2011. All of the prior applications are incorporated by reference herein this application. The present invention relates to an intravascular catheter, and more particularly to such a device that is configured to cross a totally occluded vessel.

FIELD OF THE PRESENT INVENTION

The present invention relates to an intravascular catheter, and more particularly to such a device that is configured to cross a totally occluded vessel.

BACKGROUND OF THE INVENTION

Occlusive vascular disease is generally characterized by a hardened, calcified deposit blocking the flow of blood through a blood vessel. Occlusive vascular disease can cause blockages in both coronary and peripheral blood vessels. Particularly serious examples include situations in which the lesion and deposit completely block the vessel, a condition known as chronic total occlusion (CTO). A typical CTO is a lesion located in a blood vessel of a patient that results from an accumulation of deposits, typically calcified fibrin.

Traditionally, treatment of this type of disease has required an invasive and traumatic surgical bypass of the blocked vessel. More recently, considerable effort has been invested in treating occlusive vascular disease by advancing a guidewire through or across the diseased location to create a passageway for various types of interventional procedures, including percutaneous transluminal coronary angioplasty (PTCA), atherectomy, stent delivery, and other catheter-based treatments.

Often, the true lumen of the vessel is embedded in the occlusion and is surrounded by false lumens that have been created over time. Attempts to cross the true lumen can result in the tip of the guidewire being deflected by the false lumens or off the hard cap of the occlusion into the subintimal area between the intimal layer and the adventitial layer of the blood vessel. Alternatively, a device may be deliberately guided into the subintimal area to bypass the lesion, avoiding the difficulties associated with penetrating the occlusion. Such techniques can also potentially result in a smoother passageway.

However, once the device is in the subintimal area, it can be very difficult to direct the device back into the blood vessel lumen. Currently preferred methods for these procedures involve the use of a catheter having a deflection function configured to steer the guidewire or another device back into the true lumen of the vessel. Such catheters are generally termed "re-entry" catheters.

A number of challenges are associated with the design of re-entry catheters. For example, the tip of the catheter should be held in an appropriate rotational orientation so that a passageway can be formed back into the true lumen. Further, even if most of the lesion has been bypassed, it is still often necessary to penetrate some portion of the occlusion. As a result, the re-entry catheter should minimize the difficulties in forming a passageway through a hardened lesion. Another important characteristic is the trackability and flexibility of the device. To navigate the tortuous vasculature, the device must be sufficiently flexible to allow traversal of relatively tight bends and twists. However, it is also beneficial to provide sufficient stiffness to improve the pushability of the device and to transmit torque applied to a proximal end of the device to the distal tip.

Therefore, a need remains for a medical device that can be easily positioned relative to a lesion occluding a vessel to facilitate the creation of a passageway into the true lumen from a subintimal area. It would be advantageous to provide such a device with the flexibility to be advanced through the vasculature. It would also be advantageous to provide a means to stabilize and support the device while the passageway into the true lumen is formed. As will be detailed in the discussion follows, this invention satisfies these and other goals.

SUMMARY OF THE INVENTION

In accordance with the above needs and those that will be mentioned and will become apparent below, this disclosure is directed to a re-entry catheter for facilitating formation of a passageway from a subintimal area to a lumen of a vessel, comprising an elongated outer tubular member having a distal end and a window adjacent the distal end, a plurality of deflectable struts arranged longitudinally within the window, and an actuating member coaxially disposed within the outer tubular member, wherein proximal ends of the deflectable struts are operatively connected to a distal end of the actuating member, such that axial motion of the actuating member relative to the outer tubular member deflects the struts radially outward. Preferably, the catheter has a lateral port in the outer tubular member in a location opposing the window. Also preferably, the struts are formed from a nickel-titanium alloy.

In one aspect, the window occupies a portion of the circumference outer tubular member corresponding to a range of approximately 120° to 240°.

In another aspect of the invention, tension applied to the actuating member increases stiffness at the distal end of the elongated tubular member.

As desired, the catheter can also feature a membrane supported by the struts and configured to distribute force between the struts.

Another embodiment of the invention includes a cutting member coaxially disposed within the actuating member. Preferably, the cutting member is slidably disposed within the actuating member, wherein the cutting member is configured to be advanced out of the lateral port. More preferably, the cutting member is formed from nickel-titanium alloy.

The catheters of the invention can also feature a mechanical handle operatively connected to the actuating member. Preferably, the mechanical handle configured to move the actuating member distally in an axial direction by incremental amounts.

Furthermore, currently preferred catheters have a diameter in the range of approximately 6 French and smaller.

The present disclosure is also directed to a method for forming a passageway from a subintimal area to a lumen of a vessel including the steps of providing a re-entry catheter with an elongated outer tubular member having a distal end and a window adjacent the distal end, a plurality of deflectable struts arranged longitudinally within the window, an actuating member coaxially disposed within the outer tubular member, wherein proximal ends of the deflectable struts are operatively connected to a distal end of the actuating member, and a lateral port positioned opposing the window, advancing the distal end of the catheter through a subintimal area, moving the actuating member in a distal direction to deflect the struts radially outward, and advancing a re-entry device through the lateral port and through an intimal layer of the vessel into the lumen. Preferably, moving the actuating member in a distal direction to deflect the struts radially outward engages an adventitial layer of the vessel and positions the lateral port against the intimal layer.

In one aspect, the step of advancing a device through the lateral port comprises advancing a guidewire. Alternatively, the re-entry device can be a cannula coaxially disposed within the actuating member so that the step of advancing a re-entry device through the lateral port comprises sliding the cannula through the actuating member.

Another aspect of the disclosure is directed to stiffening the distal end of the cathether by applying tension to the actuating member to facilitate navigating the distal end of the catheter through vasculature to reach the subintimal area.

A further aspect is directed to providing the catheter with a mechanical handle operative connected to the actuating member, so the method includes actuating the handle to move the actuating member distally in an axial direction by an incremental amount.

Yet another aspect of the invention includes steps of moving the actuating member in a distal direction to deflect the struts radially outward to create a space between the intimal layer and an adventitial layer and advancing the distal tip of the catheter into the space.

Further, the method can also include positioning the distal tip adjacent a lesion occluding the vessel and advancing the re-entry device so that it penetrates at least a portion of the lesion.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
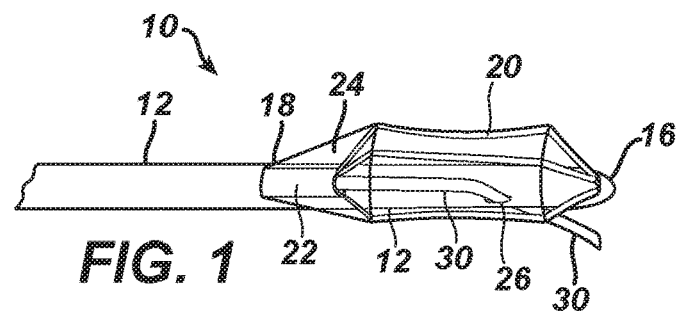
FIG. 1 is a simplified, partial elevational view of an exemplary embodiment of a re-entry catheter having an expandable distal portion, in accordance with the present invention.

At the outset, it is to be understood that this disclosure is not limited to particularly exemplified materials, architectures, routines, methods or structures as such may, of course, vary. Thus, although a number of such option, similar or equivalent to those described herein, can be used in the practice of embodiments of this disclosure, the preferred materials and methods are described herein.

It is also to be understood that the terminology used herein is for the purpose of describing particular embodiments of this disclosure only and is not intended to be limiting.

Unless defined otherwise, all technical and scientific terms used herein have the same meaning as commonly understood by one having ordinary skill in the art to which the disclosure pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise.

As known to those of skill in the art, an artery defines a true lumen surrounded by an arterial wall comprising a number of layers. The tissue of the arterial wall is collectively referred to as the extraluminal space within the artery or blood vessel. The intimal layer is the innermost layer of the arterial wall, and includes the endothelium, the subendothelial layer, and the internal elastic lamina. Adjacent the intimal layer is a medial layer followed by an adventitial layer as the outermost layer. Beyond the adventitial layer lies extravascular tissue. As used hereinafter, the region between the intimal layer and the adventitial layer, generally including the medial layer, will be referred to as the subintimal area. This disclosure is directed to the positioning of a re-entry catheter within the subintimal area so that a passageway can be formed back into the true lumen of the vessel, through which suitable intravascular devices can pass when crossing a total occlusion.

An occlusive vascular condition generally involves an atheroma, plaque, thrombus, and/or other occluding materials normally associated with cardiovascular disease. A "total" occlusion is generally considered to describe a situation in which the occluding material blocks substantially the entire lumen of the artery or other blood vessel so that blood flow through the vessel is substantially stopped. Once the occlusion has been crossed using the techniques of this disclosure, the condition can be treated using various intravascular intervention techniques, such as angioplasty, atherectomy, stenting, or the like, to restore blood flow through the affected vessel.

The re-entry catheter of the present invention employs deflectable struts to stabilize and support the distal tip in a subintimal location while a passageway back into the true lumen is formed. Re-entry to the true lumen can be effected with a cutting element or with a conventional guidewire. Another feature of the re-entry catheters of this disclosure is that the relative flexibility of the distal tip can be varied depending upon the amount of force exerted on the deflectable struts. These features and others can be recognized more clearly with regard to the exemplary embodiments discussed below.

Turning now to FIGS. 1-5, a distal portion of re-entry catheter 10 having features according to the invention is schematically depicted in a variety of views and configurations, some partially in section. Re-entry catheter 10 comprises an outer elongated tubular member 12. Outer tubular member 12 terminates at a distal end in nosecone 16, which preferably has a tapered configuration to facilitate advancement through the vasculature.

Outer tubular member 12 also features a window 18 formed at the distal end adjacent nosecone 16. A plurality of deflectable struts 20 are longitudinally arranged within the window 18. Currently preferred embodiments include at least three struts 20. The distal ends of struts 20 are secured at nosecone 16. The proximal ends of struts 20 are operatively connected to and configured to be displaced axially by actuating member 22, causing them to deflect. In this embodiment, actuating member 22 comprises a hypotube or other similar structure, that is coaxially disposed within outer tubular member 12. Actuating member 22 is configured to slide axially relative to outer tubular member 12, so that moving the proximal end of actuating member 22 in a distal direction transmits a pushing force to the proximal ends of struts 20, bowing them outwards to radially expand at window 18. As desired, struts 20 can be covered with membrane 24 to help distribute force to areas between struts 20. Membrane 24 can be disposed over struts 20, secured to inside of struts 20, or be supported by other suitable means. Membrane is preferably formed polytetrafluroethylene, but can also be formed from other biocompatible materials, including elastic polymers, such as silicones, polyamides, nylons, or a polyolefin such as polyethylene.

Lateral port 26 on outer tubular member 12 opposes window 18. A cutting member configured to penetrate an occluding lesion, such as re-entry cannula 30, is slidably disposed within inner tubular member 14, so that it can be advanced through port 26 at a suitable angle with respect to the longitudinal axis of catheter 10. By penetrating the intimal vessel wall, a passageway into the true lumen can be formed.

Figure 2:
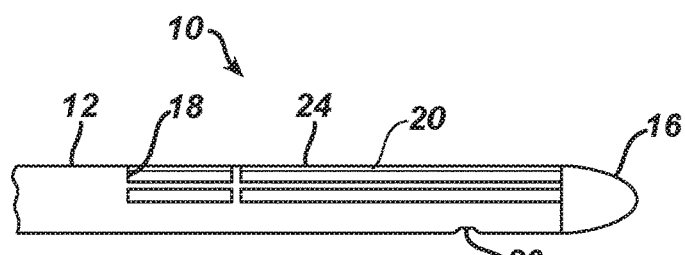
FIG. 2 is a view of the embodiment shown in FIG. 1 in a relaxed configuration, according to the invention.
Figure 3:
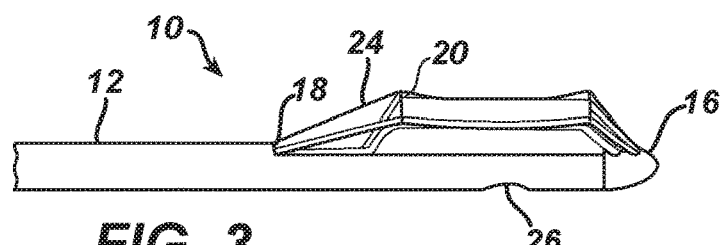
FIG. 3 is a view of the embodiment shown in FIG. 1 in an expanded configuration, according to the invention.
Figure 4:
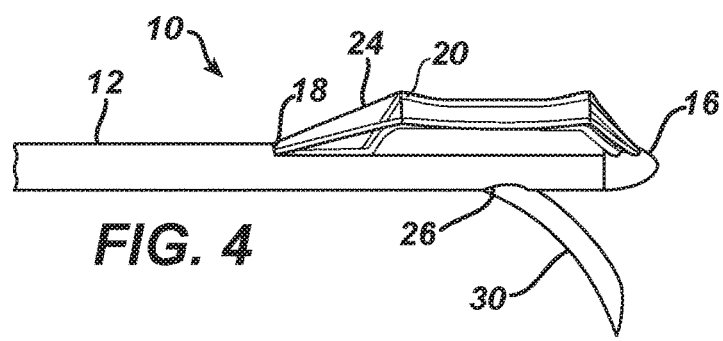
FIG. 4 is a view of the embodiment shown in FIG. 1 in an expanded configuration, with a re-entry cannula advanced, according to the invention.

As can be seen, FIG. 2 shows struts 20 in a relaxed, unexpanded state, lying parallel to and contiguous with the outer tubular member 12, thus presenting a uniform profile to allow catheter 10 to be advanced through the vasculature. FIG. 3, on the other hand, shows struts 20 in a deflected, expanded state. The deflection of struts 20 generally acts to engage the adventitial layer of the vessel, so that lateral port 26 is held against the intimal layer, stabilizing and supporting catheter 10 as cannula 30 is advanced as shown in FIG. 4.

Figure 5:
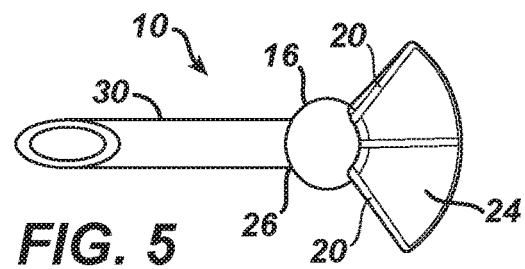
FIG. 5 is a cross sectional view of the embodiment shown in FIG. 1, in an expanded configuration, with a re-entry cannula advanced, according to the invention.
Figure 6:
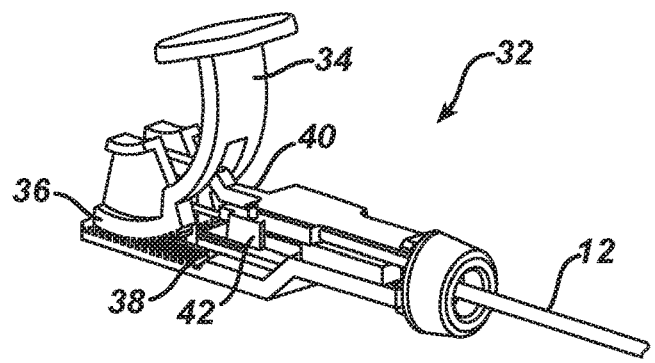
FIG. 6 is a schematic, elevational view of the proximal end of a re-entry catheter showing a mechanical handle, according to the invention.

A cross sectional view of catheter 10 is shown in FIG. 5. Lateral port 26 is positioned opposite window 18 on outer tubular member 12. This configuration maximizes the support offered by the expansion of struts 20 to facilitate the advancement of cannula 30 through a potentially hardened lesion. Further, membrane 24 helps distribute pressure along the circumference formed by the expansion of struts 20. In the embodiment shown, window 18 and struts 20 occupy approximately 120° of the circumference of outer tubular member 12. As will be discussed below, other configurations can also be employed as desired.

As discussed, actuating member 22 transmits axial force to struts 20. A sufficient compressive force will cause struts 20 to bow radially outwards, expanding a portion of catheter 10 adjacent window 18. Additionally, actuating member 22 can also transmit other degrees of axial force to struts 20. For example, a compressive force less than the threshold that would deflect struts 20 can be applied. The resulting tension in struts 22 stiffens the distal tip of catheter 10 relative to the state when no tension is applied to struts 22. Conversely, a retracting force can be applied to struts 20 by pulling actuating member 22 in a proximal direction. When struts 20 are fully retracted, the application of this force tensions struts 20 and causes a relative increase in stiffness. Accordingly, one of skill in the art will recognize that the operator can apply varying degrees of tension in either a proximal or distal direction to affect the flexibility of the distal tip of catheter 10, facilitating navigation through the vasculature.

Preferably, actuating member 22 is driven by a mechanical handle 32 at the proximal end of catheter. For example, lever 34 has a pinion portion 36 engaged with rack 38. Depressing lever 34 causes pinion 36 to travel along rack 38, thus driving pushing member 40 in a distal direction. Pushing member 40 is operatively connected to actuating member 22, so that operation of lever 34 is translated into axial motion configured to deflect struts 20. A ratchet 42 is configured to engage pushing member 40, holding it at a desired position until released. As will be appreciated, the mechanical nature of handle 32 gives the operator direct, tactile feedback regarding the amount of force being transmitted to struts 20 via actuating member 22. This configuration also allows the operator to make incremental adjustments to the amount of expansion caused by the deflection of struts 20.

Figure 7:
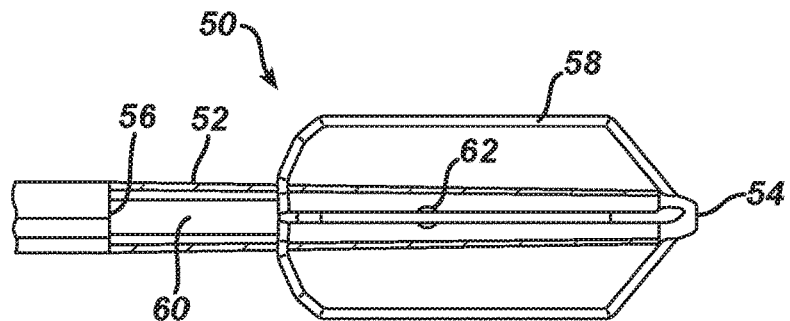
FIG. 7 is a simplified, partial cross sectional view of another exemplary embodiment of a re-entry catheter having a expandable distal portion, in accordance with the present invention.

Another embodiment of the invention is shown in FIG. 7, which generally includes re-entry catheter 50 having elongated tubular member 52 terminating at a distal end in nosecone 54, which preferably has a tapered configuration to facilitate advancement through the vasculature. Outer tubular member 52 has a window 56 formed at the distal end adjacent nosecone 54. A plurality of deflectable struts 58 are longitudinally arranged within the window 56. The distal ends of struts 58 are secured at nosecone 54. The proximal ends of struts 20 are operative connected to and configured to be displaced axially by actuating member 60, causing them to deflect. In this embodiment, actuating member 22 comprises a hypotube coaxially disposed within outer tubular member 52. Actuating member 60 is configured to slide axially relative to outer tubular member 52. Distal motion of actuating member 60 bows struts 58 outward, radially expanding the distal end of catheter 50 at window 56. Lateral port 62 on outer tubular member 52 opposes window 54. Preferably, lateral port 62 is configured to redirect a guidewire advanced through actuating member 60 in a lateral direction, so that the tip of the guidewire will penetrate the intimal wall and access the true lumen of the vessel.

Figure 8:
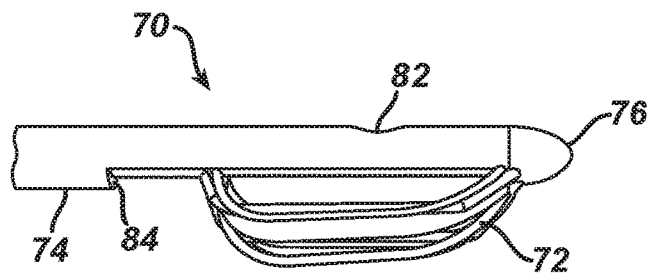
FIG. 8 is a simplified, elevational view of another exemplary embodiment of a re-entry catheter having a expandable distal portion, in accordance with the present invention, according to the invention.
Figure 9:
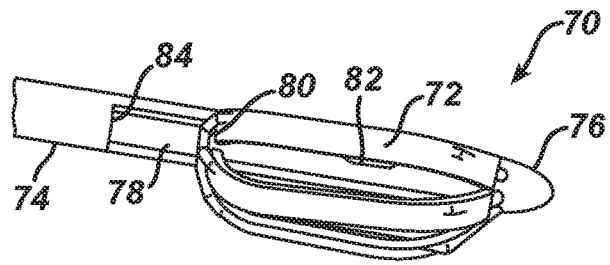
FIG. 9 is a view of the embodiment shown in FIG. 8, according to the invention.

Next, yet another embodiment of the invention is shown in FIGS. 8 and 9. Similar to the embodiment shown in FIG. 7, catheter 70 features a plurality of deflectable struts 72 arranged at the distal end of outer tubular member 74. Struts 72 are configured to present a wider profile to provide a more even distribution of the force exerted when they are deflected into an expanded configuration. Struts 72 are secured at their distal ends by nosecone 76. The proximal ends of struts 72 are secured to an elongated tubular actuating member 78, slidably disposed within outer tubular member 74. A guidewire advanced through the lumen 80 of actuating member 78 is configured to be directed through lateral port 82 towards the vessel's lumen when catheter 70 is positioned in a subintimal area. If desired, struts 72 can have a wider profile to increase distribution of pressure. For example, struts 72 can be configured so that their edges are adjacent or touching when expanded. In such embodiments, struts 72 overlap when in a relaxed, unexpanded configuration. Struts 72 are disposed within window 84 formed in the distal end of outer tubular member 74.

In generally, the components of the invention can be formed from conventional materials, including metals such as stainless steel, polymers such as polyethylenes and composite materials. As will be discussed below, shape memory nickel-titanium alloys are preferred for the struts and re-entry cannula.

Figure 10:
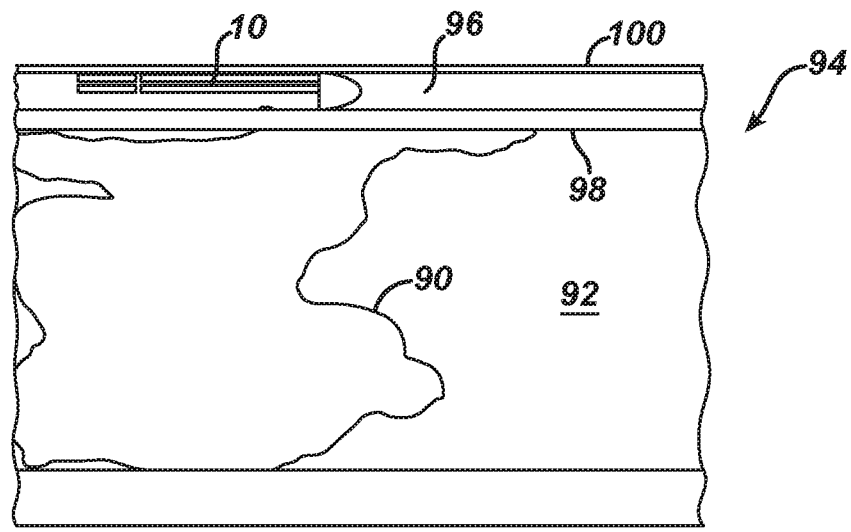
FIG. 10 is a schematic view of a re-entry catheter positioned adjacent an occluding lesion, according to the invention.

FIGS. 10-14 show various aspects of the operation of the re-entry catheters of the invention with respect to a lesion 90 that is totally occluding the lumen 92 of blood vessel 94. Although catheter 10 is the embodiment shown, it will be recognized that any of the exemplary embodiments discussed herein or other embodiments having features of the invention can be employed in similar manners. As shown in FIG. 10, catheter 10 is being advanced in a subintimal area 96 between intimal layer 98 and adventitial layer 100. As desired, struts 20 can be expanded to create space between intimal layer 98 and adventitial layer 100, facilitating advancement of catheter 10.

Figure 11:
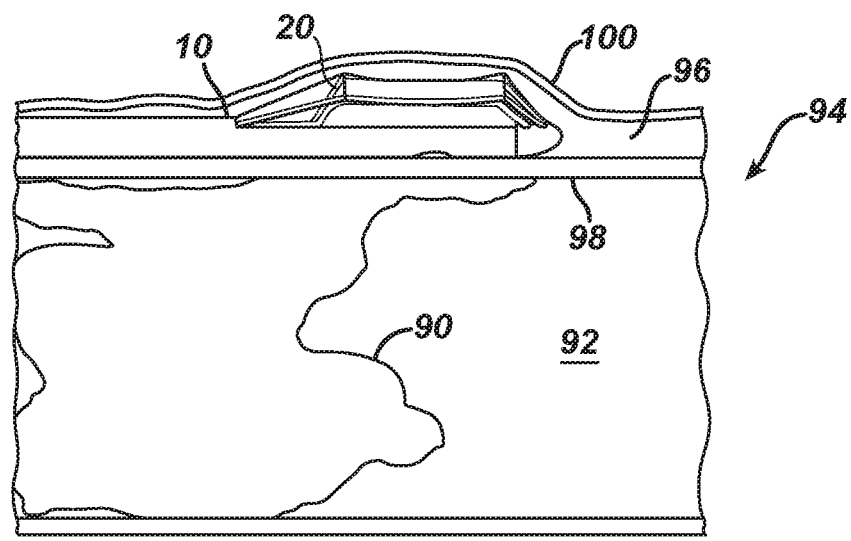
FIG. 11 is a schematic view of a re-entry catheter in an expanded state positioned adjacent an occluding lesion, according to the invention.

Once the distal tip of catheter 10 has been advanced a sufficient distance beyond lesion 90, actuating member 22 is moved axially in a distal direction, causing struts 20 to deflect radially outwards as shown in FIG. 11. Membrane 24 distributes the force being exerted against adventitial layer 100. As discussed above, expansion of struts 20 stabilizes catheter 10 so that lateral port 26 is held against intimal layer 98

Figure 12:
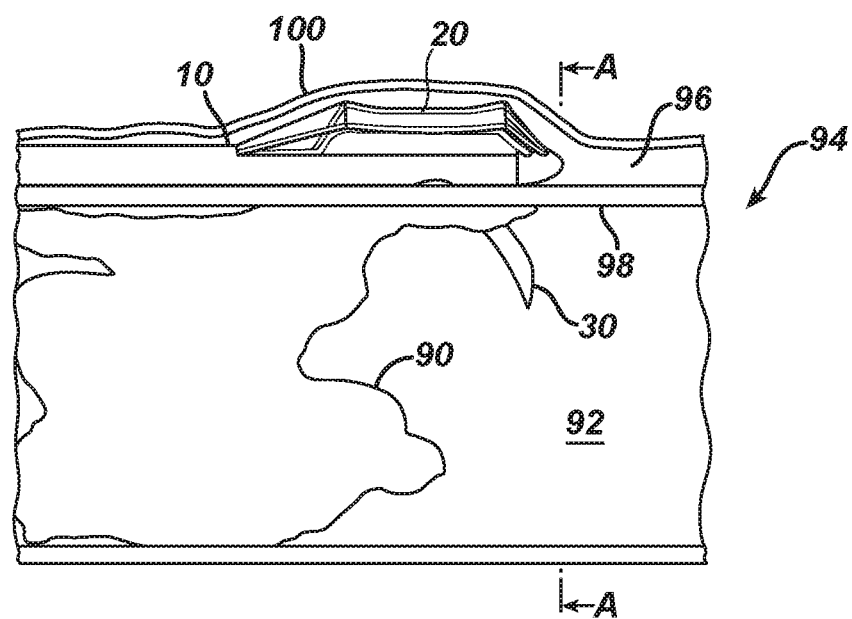
FIG. 12 is a schematic view of a re-entry catheter in an expanded state, showing re-entry into the true lumen with an actuated cannula, according to the invention.

After catheter 10 is supported by the expansion of struts 20, cannula 30 can be advanced out lateral port 26 as shown in FIG. 12. In some cases, it will be necessary to penetrate a portion of lesion 90 in addition to intimal layer 98 to access lumen 92. When lesion 90 is calcified or hardened, it can offer substantial resistance to the advancement of cannula 30. Expansion of struts 20 allows catheter 10 to engage a wide area of adventitial layer 100 to help provide the necessary support so that cannula 30 can be pushed through lesion 90 without losing alignment or orientation.

Figure 13:
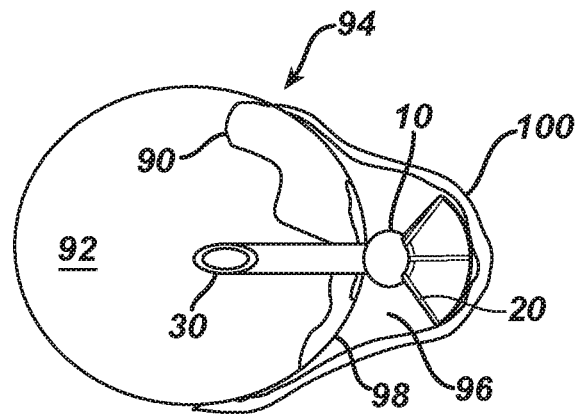
FIG. 13 is a cross sectional view of the re-entry catheter shown in FIG. 12, taken at line A-A, according to the invention.

FIG. 13 shows a cross section taken at line A-A from FIG. 12. As can be seen, expansion of struts 20 provides catheter 10 with a profile configured to fit within the geometry of the displaced adventitial layer 100. This helps align lateral port 26 substantially perpendicular to lumen 92. Preferably, the improved orientation helps minimize any visualization requirement. Further, the increased area presented by the expansion of struts 20 engages a greater portion of adventitial layer 100. Without such expansion, the narrower profile of a catheter alone has a greater tendency to be pushed back into the relatively elastic layer when penetration of a hardened lesion is attempted.

Figure 14:
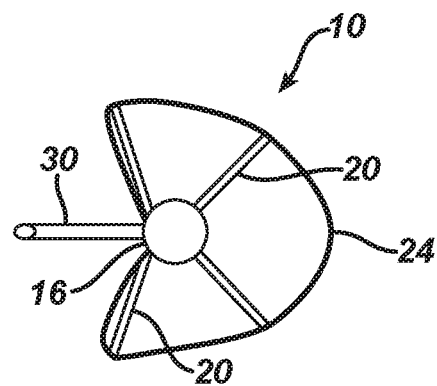
FIG. 14 is a cross sectional view of yet another exemplary embodiment of a re-entry catheter, according to the invention.

As shown in FIG. 13, struts 20 and window 18 correspond to approximately 120° of the circumference of outer tubular member 12. In a further aspect of the invention, the proportion of circumference occupied by struts 20 can be varied to alter the performance characteristics. For example, in another embodiment, struts 20 and window 18 correspond to approximately 240° of the circumference of outer tubular member 12. as shown in FIG. 14. In general, the portion occupied by window 18 can be in the range of approximately 90° to 270°. As will be appreciated, such embodiments can provide a closer fit within the space formed by the separation of adventitial layer 100 from intimal layer 98.

Another aspect of the disclosure is the reduction in overall diameter that can be achieved using the catheters disclosed herein. Due to the increased support offered by the expansion of the deflectable struts, less structural rigidity is required to maintain the ability to resist counter forces when penetrating the lesion. Further, the increased support also permits the use of smaller guidewires, such as 0.14" guidewires. Presently preferred embodiments include catheters having a French size of 6 and below. Similarly, the catheters can have improved flexibility, allowing a greater range of areas to be accessed. When increased stiffness is required for pushability, tension can be applied to the deflectable struts as described above. Further reductions in diameter can be achieved by employing embodiments such as catheters 50 and 70 which do not feature a re-entry cannula. For example, one embodiment of the invention has a diameter of 3 French and has sufficient flexibility to navigate the iliac bifurcation to allow a contralateral approach to superficial femoral artery locations. As will be appreciated, such an embodiment can be used to access tibial and other below-knee areas. Embodiments having reduced diameters can also be suitable for coronary applications.

In presently preferred embodiments of the invention, struts 20, 58 or 72, are formed from a nickel-titanium alloy such as Nitinol. Also preferably, cannula 30 can be formed from a nickel-titanium alloy. As known to those of skill in the art, these alloys can exhibit shape memory and/or superelastic characteristics. Generally, shape memory allows the member to be deformed to secondary configuration, but when heated will return to its original configuration. Superelastic characteristics, on the other hand, generally allow the metal to be placed under strain and deformed, causing a phase transformation. Once the strain is removed, the superelastic member will change phase and return to its original shape. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal to a temperature above which the transformation from the martensite phase to the austenite phase is complete, i.e. a temperature above which the austenite phase is stable (the Af temperature). The shape of the metal during this heat treatment is the shape "remembered." The heat-treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape if unrestrained. If restrained, the metal will remain martensitic until the restraint is removed.

When stress is applied to a specimen of a metal, such as Nitinol, exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity.

One of skill in the art will recognize that the above properties are particularly suitable to the deflection of struts 20, 58 and 72 from their relaxed, unexpanded state to the bowed-out, expanded configuration. Similarly, cannula 30 can be restrained in a straight configuration prior to actuation and can assume a curved profile to aim more directly at the true lumen as it is advanced out lateral port 26.

It some situations it may be necessary to determine the position of the devices of the invention with respect to the total occlusion so that a passageway can be formed returning to the true lumen of the blood vessel. Most simply, such position determination can be made by fluoroscopically imaging the blood vessel in a conventional manner. Alternatively or additionally to such fluoroscopic imaging, intravascular imaging, e.g. intravascular ultrasonic imaging (IVUS), and a variety of optical imaging modelities, such as optical coherence tomography (OCT), may be employed. For example, an ultrasonic imaging guidewire may be used to initially access the subintimal area and/or may be exchanged for the wire which is used to access the subintimal area. An imaging guidewire present in the subintimal area may readily detect the presence or absence of occluding material within the blood vessel lumen. When the transition from occluding material to lack of occluding material is detected, it is known that the position of the guidewire has advanced beyond the total occlusion.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A re-entry catheter for facilitating formation of a passageway from a subintimal area to a lumen of a vessel, comprising an elongated outer tubular member configured to be disposed in the subintimal area between an intimal layer and an adventitial layer, the elongated outer tubular member having a distal end and a window adjacent the distal end, a plurality of deflectable struts arranged longitudinally within the window, a lateral port in the outer tubular member in a location opposing the window, and an actuating member coaxially disposed within the elongated outer tubular member and configured for axial motion relative to the elongated outer tubular member, a cutting member comprising a cannula coaxially disposed within the actuating member, wherein proximal ends of the plurality of deflectable struts are operatively connected to a distal end of the actuating member, such that axial motion of the actuating member deflects the plurality of deflectable struts radially outward so that the lateral port is held against the intimal layer as the cannula advances out of the lateral port and into a lesion disposed in the lumen of the vessel.

2. The re-entry catheter of claim 1, wherein the struts are formed from a nickel-titanium alloy.

3. The re-entry catheter of claim 1, wherein the outer tubular member has a circumference and wherein the window occupies a portion of the circumference corresponding to a range of approximately 120° to 240°.

4. The re-entry catheter of claim 1, wherein tension applied to the actuating member increases stiffness at the distal end of the elongated tubular member.

5. The re-entry catheter of claim 1, further comprising a membrane supported by the struts and configured to distribute force between the plurality of deflectable struts.

6. The re-entry catheter of claim 1, wherein the cannula is formed from nickel-titanium alloy.

7. The re-entry catheter of claim 1, wherein the actuating member is operatively connected to a mechanical handle configured to move the actuating member distally in an axial direction by incremental amounts.

8. The re-entry catheter of claim 1, wherein the catheter has a diameter in the range of approximately 6 French and smaller.

9. The re-entry catheter of claim 1, wherein the cutting member is slidably disposed within the actuating member.

10. The re-entry catheter of claim 1, wherein the actuating member comprises a hypotube coaxially disposed within the outer tubular member.

11. The re-entry catheter of claim 1, wherein the lateral port is located diametrically opposed to the window.

\* \* \* \* \*